(12) United States Patent
Li et al.

(10) Patent No.: US 10,160,954 B2
(45) Date of Patent: *Dec. 25, 2018

(54) ENGINEERED PHYSICAL ALIGNMENT OF STEM CELL-DERIVED CARDIOMYOCYTES

(71) Applicant: The Regents of the University of California, Oakland, CA (US)

(72) Inventors: Ronald Li, New York, NY (US); Michelle Khine, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 286 days.

This patent is subject to a terminal disclaimer.

(21) Appl. No.: 14/762,777

(22) PCT Filed: Jan. 23, 2014

(86) PCT No.: PCT/US2014/012816
§ 371 (c)(1),
(2) Date: Jul. 22, 2015

(87) PCT Pub. No.: WO2014/116874
PCT Pub. Date: Jul. 31, 2014

(65) Prior Publication Data
US 2015/0353894 A1 Dec. 10, 2015

Related U.S. Application Data

(60) Provisional application No. 61/755,871, filed on Jan. 23, 2013.

(51) Int. Cl.
C12N 5/077 (2010.01)

(52) U.S. Cl.
CPC ...... *C12N 5/0657* (2013.01); *C12N 2501/155* (2013.01); *C12N 2501/16* (2013.01); *C12N 2501/415* (2013.01); *C12N 2506/02* (2013.01); *C12N 2535/00* (2013.01); *C12N 2535/10* (2013.01)

(58) Field of Classification Search
None
See application file for complete search history.

(56) References Cited

U.S. PATENT DOCUMENTS

| | | | |
|---|---|---|---|
| 5,733,761 A | 3/1998 | Treco et al. | |
| 6,638,369 B1 | 10/2003 | Tucker et al. | |
| 9,045,731 B2 | 6/2015 | Li et al. | |
| 2004/0254134 A1 | 12/2004 | Marban et al. | |
| 2005/0042254 A1 | 2/2005 | Freyman et al. | |
| 2005/0058633 A1 | 3/2005 | Epstein et al. | |
| 2007/0161107 A1 | 7/2007 | Mummery et al. | |
| 2008/0089874 A1 | 4/2008 | Li et al. | |
| 2009/0317852 A1* | 12/2009 | Parker .................. | C12N 5/0062 435/29 |
| 2011/0122406 A1 | 5/2011 | Khine et al. | |
| 2012/0027807 A1 | 2/2012 | Chien et al. | |
| 2012/0129208 A1 | 5/2012 | Khine et al. | |
| 2012/0129209 A1 | 5/2012 | Khine et al. | |
| 2012/0200008 A1 | 8/2012 | Khine et al. | |
| 2013/0040335 A1 | 2/2013 | Khine et al. | |
| 2013/0101795 A1 | 4/2013 | Khine et al. | |
| 2013/0309450 A1 | 11/2013 | Khine et al. | |
| 2013/0330378 A1* | 12/2013 | Parker .................... | A61K 35/34 424/400 |
| 2014/0094388 A1* | 4/2014 | Wakatsuki ........... | C12N 5/0627 506/9 |
| 2015/0125952 A1* | 5/2015 | Kim ........................ | A61L 27/14 435/366 |
| 2015/0218549 A1 | 8/2015 | Li et al. | |
| 2016/0045555 A1 | 2/2016 | Li et al. | |

FOREIGN PATENT DOCUMENTS

| | | |
|---|---|---|
| WO | WO-02/087419 A2 | 11/2002 |
| WO | WO-2006/017566 A2 | 2/2006 |
| WO | WO-2006/017567 A2 | 2/2006 |
| WO | WO-2009/036220 A2 | 3/2009 |
| WO | WO-2009/064816 A1 | 5/2009 |
| WO | WO-2009/152482 A2 | 12/2009 |
| WO | WO-2011/028579 A2 | 3/2011 |
| WO | WO 2012/115658 A1 | 8/2012 |

OTHER PUBLICATIONS

Bursac, N., et al. "Cardiomyocyte cultures with controlled macroscopic anisotropy." Circulation research 91.12 (2002): e45-e54.*
Bettinger, C.J. et al. (2009) "Engineering Substrate Micro- and Nanotopography to Control Cell Function," Angew Chem Int Ed Engl. 48(30):5406-5415.
Karakikes, I. et al. (2014) "Small Molecule-Mediated Directed Differentiation of Human Embryonic Stem Cells Toward Ventricular Cardiomyocytes," Stem Cells Translational Medicine 3:18-31.
Lieu, D.K. et al. (2013) "Mechanism-Based Facilitated Maturation of Human Pluripotent Stem Cell-Derived Cardiomyocytes," Circ Arrhythm Electrophysiol. 6:191-201.
Poon, E. et al. (2011) "Human Pluripotent Stem Cell-Based Approaches for Myocardial Repair: From the Electrophysical Perspective," Mol Pharmacol. 8:1495-1504.
Luna, J.I. et al. (2011) "Multiscale Biomimetic Topography for the Alignment of Neonatal and Embryonic Stem Cell-Derived Heart Cells," Tissue Engineering: Part C, 17(5):579-588.
Wang, J. et al. (2013) "Effect of engineered anisotropy on the susceptibility of human pluripotent stem cell-derived ventricular cardiomyocytes to arrhythmias," Biomaterials 34(35):8878-8886.
Extended European Search Report for European Application No. 14743690.1, dated Jun. 9, 2016.
Chen, A. et al. (2011) "Shrink-Film Configurable Multiscale Wrinkles for Functional Alignment of Human Embryonic Stem Cells and Their Cardiac Derivatives," Advanced Materials, 23:5785-5791.
International Search Report and Written Opinion (ISA/US) for International Application No. PCT/US2014/012816, dated Apr. 18, 2014, 18 pages.

(Continued)

*Primary Examiner* — Robert J Yamasaki
(74) *Attorney, Agent, or Firm* — Nguyen & Tarbet Law Firm

(57) ABSTRACT

Provided are devices and methods of preparing a population of cardiomyocytes by aligning undifferentiated pluripotent cells on a nanosacale textured surface.

22 Claims, 5 Drawing Sheets

(56) References Cited

OTHER PUBLICATIONS

Abraham, M.R. et al. (2005) "Antiarrhythmic engineering of skeletal myoblasts for cardiac transplantation," Circ. Res. 97(2):159-167.
Au, H.T.H. et al. (2007) "Interactive effects of surface topography and pulsatile electrical field stimulation on orientation and elongation of fibroblasts and cardiomyocytes," Biomaterials 28:4277-4293.
Baharvand, H. et al. (2005) "The effect of extracellular matrix on embryonic stem cell-derived cardiomyocytes," Journal of Molecular and Cellular Cardiology 38:495-503.
Beqqali, A. et al. (2006) "Genome-Wide Transcriptional Profiling of Human Embryonic Stem Cells Differentiating to Cardiomyocytes," Stem Cells 24:1956-1967.
Boheler, K.R. et al. (2002) "Differentiation of Pluripotent Embryonic Stem Cells Into Cardiomyocytes," Circulation Research 91:189-201.
Boheler, K.R. et al. (2011) "Embryonic Stem Cell-Derived Cardiomyocyte Heterogeneity and the Isolation of Immature and Committed Cells for Cardiac Remodeling and Regeneration," Stem Cells International 2011(Article ID 214203:: pp. 1-10.
Chan, Y-C. et al. (2010) "Automaticity and conduction properties of bio-artificial pacemakers assessed in an in vitro monolayer model of neonatal rat ventricular myocytes," Eurospace 12:1178-1187.
Dolnikov, K. et al. (2005) "Functional properties of human embryonic stem cell-derived cardiomyocytes," Ann. N.Y. Acad. Sci. 1047:66-75.
Dolnikov, K. et al.(2006) "Functional Properties of Human Embryonic Stem Cell-Derived Cardiomyocytes: Intracellular Ca2 Handling and the Role of Sarcoplasmic Reticulum in the Contraction," Stem Cells 24:236-245.
Fu, J-D. et al. (2006) "Developmental regulation of intracellular calcium transients during cardiomyocyte differentiation of mouse embryonic stem cells," Acta Pharmacologica Sinica 27(7):901-910.
Halbach, M. et al. (2007) "Electrophysiological Maturation and Integration of Murine Fetal Cardiomyocytes After Transplantation," Circ Res. 101:484-492.
He, J-Q. et al. (2003) "Human Embryonic Stem Cells Develop Into Multiple Types of Cardiac Myocytes," Circ. Res. 93:32-39.
Huber, I. et al. (2007) "Identification and selection of cardiomyocytes during human embryonic stem cell differentiation," The FASEB Journal 21:2551-2563.
Itzhaki, I. et al. (2006) "Calcium Handling in Embryonic Stem Cell-Derived Cardiac Myocytes of Mice and Men," Ann. New York Academy of Sciences 1080:207-215.
Kehat, I. et al. (2001) "Human embryonic stem cells can differentiate into myocytes with structural and functional properties of cardiomyocytes," J. Clin. Invest. 108:407-414.
Kolossov, E. et al. (1998) "Functional Characteristics of ES Cell-derived Cardiac Precursor Cells Identified by Tissue-specific Expression of the Green Fluorescent Protein," The Journal of Cell Biology 143(7):2045-2056.
Li, R.A. et al. (2005) "Human embryonic stem cell-derived cardiomyocytes: therapeutic potentials and limitations," Journal of Stem Cells 1(2):109-124.
Lieu, D.K. et al. (2013) "Mechanism-Based Facilitated Maturation of Human Pluripotent Stem Cell-Derived Cardiomyocytes," Circulation: Arrhythmia and Electrophysiology:1-25.
Liu, J. et al. (2007) "Functional Sarcoplasmic Reticulum for Calcium Handling of Human Embryonic Stem Cell-Derived Cardiomyocytes: Insights for Driven Maturation," Stem Cells 25:3038-3044.
Moore, J.C. et al. (2005) "Human embryonic stem cells: Genetic manipulation on the way to cardiac cell therapies," Reproductive Toxicology 20:377-391.
Mummery, C. et al. (2002) "Differentiation of Human Embryonic Stem Cells to Cardiomyocytes," Circulation 107:2733-2740.
Radisic, M. et al. (2004) "Functional assembly of engineered myocardium by electrical stimulation of cardiac myocytes cultured on scaffolds," PNAS 101(52):18129-18134.
Sartiani, L. et al. (2007) "Developmental Changes in Cardiomyocytes Differentiated from Human Embryonic Stem Cells: A Molecular and Electrophysiological Approach," Stem Cells 25:1136-1144.
Satin, J. et al. (2004) "Mechanism of spontaneous excitability in human embryonic stem cell derived cardiomyocytes," J Physiol. 559(2):479-496.
Satin, J. et al. (2008) "Calcium Handling in Human Embryonic Stem Cell-Derived Cardiomyocytes," Stem Cells 26:1961-1972.
Sauer, H. et al. (2001) "Characteristics of calcium sparks in cardiomyocytes derived from embryonic stem cells," Am J Physiol Heart Cir Physiol. 281:H411-H421.
Siu, C.W. et al. (2006) "HCN-Encoded Pacemaker Channels: From Physiology and Biophysics to Bioengineering," J. Membrane Biol. 214(3):115-122.
Siu, C.W. et al. (2007) "Human Embryonic Stem Cell-Derived Cardiomyocytes for Heart Therapies," Cardiovascular & Haematological Disorders—Drug Targets 7(2):145-152.
Smits, P.C. (2004) "Myocardial repair with autologous skeletal myoblasts: a review of the clinical studies and problems," Minerva Cardioangiol. 52:525-535.
Tomita, Y. et al. (2007) "Application of mesenchymal stem cell-derived cardiomyocytes as bio-pacemakers: current status and problems to be solved," Med. Bio. Eng. Comput. 45:209-220.
Wang, K.W. et al. (2005) "Electrophysiological Properties of Pluripotent Human and Mouse Embryonic Stem Cells," Stem Cells 23(10):1526-1534.
Wobus, A.M. et al. (2002) "Embryonic stem cells as a model to study cardiac, skeletal muscle, and vascular smooth muscle cell differentiation," Methods in Molecular Biology 185:127-156.
Xu, C. et al. (2002) "Characterization and Enrichment of Cardiomyocytes Derived From Human Embryonic Stem Cells," Circulation Research 91:501-508.
Xue, T. et al. (2005) "Functional integration of electrically active cardiac derivatives from genetically engineered human embryonic stem cells with quiescent recipient ventricular cardiomyocytes: insights into the development of cell-based pacemakers," Circulation 111(1):11-20.
Yang, L. et al. (2008) "Human cardiovascular progenitor cells develop from a KDR+ embryonic-stem-cell-derived population," Nature 453:524-528.
Zhang, Y.M. et al. (2002) "Stem cell-derived cardiomyocytes demonstrate arrhythmic potential," Circulation 106:1294-1299.
U.S. Notice of Allowance dated May 21, 2018, from U.S. Appl. No. 14/615,291.

\* cited by examiner

ENGINEERED PHYSICAL ALIGNMENT OF STEM CELL-DERIVED CARDIOMYOCYTES

CROSS-REFERENCE TO RELATED APPLICATIONS

This application is a national phase application under 35 U.S.C. § 371 of International Application No. PCT/US2014/012816, filed Jan. 23, 2014, which in turn claims the benefit under 35 U.S.C. § 119(e) to U.S. provisional application No. 61/755,871, filed Jan. 23, 2013, the contents of each of which are incorporated here by reference in their entirety.

STATEMENT AS TO FEDERALLY SPONSORED RESEARCH OR DEVELOPMENT

This invention was made with government support under the National Institute of Health, Faculty Core, Research Grant Council, Grants GRF 103544 and TBRS T23-706/11. Accordingly, the U.S. Government has certain rights to the invention.

BACKGROUND

Ventricular fibrillation (VF) is the most common cause for sudden death in adults; heart failure patients are particularly prone to VF. The generation of VF requires both a cellular trigger (e.g., action potential prolongation, early and delayed after depolarizations) as well as multi-cellular reentrant events (e.g., spiral wave reentry). Human pluripotent stem cells (PSC) such as hESC can be directed into the cardiac lineage with high efficiency, presenting a potential unlimited source of cardiomyocytes (CMs) for cell-based myocardial repair.

Their functional efficacy and safety, in terms of their arrhythmogenicity, however, have not been thoroughly assessed. Indeed, hESC-CMs are known to be functionally immature at the single-cell level, and as such may serve as substrates for arrhythmias in multi-cellular preparations.

In the native heart, ventricular (V) CMs are aligned in a highly organized manner such that the conduction of electrical signals is anisotropic (i.e. asymmetrical, with distinct transverse and longitudinal velocities) for coordinated, directional electrical and contractile activities. By contrast, hESC-CM clusters differentiated in vitro using either embryoid body (EB) formation or directed. differentiation are randomly organized and isotropic.

There is a need, therefore, to develop technologies to in vitro differentiate pluripotent stem cells into CMs producing more anisotropic electrical signals and having more coordinated, directional electrical and contractile activities.

SUMMARY

The present disclosure presents data to demonstrate that, using shrink-film microgroove technology, sheets of aligned hESC-VCM preparations can be generated, followed by high-resolution optical mapping recordings to examine in detail their action potential (AP) and conduction velocity (CV) properties. These results lay the foundation for designing PSC-derived grafts with superior functional efficacy and safety, as well as accurate human cardiac assays for disease modeling and arrhythmogenicity screening.

The present disclosure, in some embodiments, provides a method for growing and/or differentiating cells to cardiomyocytes, wherein the cells are physically aligned and produce functional anisotropy and less susceptible to reentrant arrhythmias. Importantly, such preparations better mimic the organization of the native heart thereby serving as a more accurate model. The cell population is minimally heterogeneous, e.g., less than 50% heterogeneous in cell type. The populations are prepared by a stem cell or its derivative(s) on a substrate having a textured surface, wherein the textured surface is prepared by a method described herein. In one aspect, the textured surface is treated with an extracellular matrix prior to culturing the cells. In one aspect, the method further comprises removing the cells from the substrate. Still further provided is a population of cells produced by the method on the substrate or alternatively, removed from the substrate.

In some embodiments, provided is a method of preparing a plurality of aligned cardiomyocytes, comprising culturing a stem cell on a textured surface under conditions suitable for the stem cell to differentiate into cardiomyocytes, thereby preparing a plurality of aligned cardiomyocytes, wherein the textured surface is prepared with a preparation method comprising treating a thermoplastic material with plasma, shrinking the treated thermoplastic material to obtain a textured surface, and replicating the textured surface using soft lithography to a scaffold to generate a textured surface on the scaffold.

In one aspect, the method further comprises, prior to culturing the stem cell on the textured surface, preparing the textured surface with the preparation method. In one aspect, the thermoplastic material is treated with the plasma for a time between about 3 and 15 minutes, or between about 4 minutes and 10 minutes, between about 4 minutes and 8 minutes, or of about 5 minutes.

In one aspect, only one side of the thermoplastic material is treated with the plasma, while the other side is not. In one aspect, the plasma is oxygen plasma.

In some embodiments, provided is an isolated population of cardiomyocytes prepared by aligning stem cells on a concave micro-textured surface. In some aspects, the population comprises ventricular cardiomyocytes (VCM). In some aspects, the population comprises ventricular cardiomyocytes and fibroblasts. In one aspect, the population comprises VCM:fibroblasts in a ratio of the group selected from 1:0; 1:1; 2:1; and 1:2.

In some aspects, the textured surface is concave, such as an interior portion of a chamber or balloon. It is observed that such a three-dimensional structure, in addition to the micro texture, further improves desirable differentiation of the stem cells, e.g., into ventricular cardiomyocytes. In some aspects, the concave textured surface has a horizontally flat edge. In some aspects, the edge is round or oval. In some aspects, the concave textured surface includes at least about 10% of a sphere, or at least about 20%, 30%, 40%, 50%, 60%, 70%, 80% or 90% of a sphere. In some aspects, the concave surface is part of a chamber or balloon. In some aspects, the concave has a radius that is at least about 1 cm, or 2 cm, 5 cm, 10 cm or no more than about 100 cm, 50 cm, 20 cm, 10 cm or 5 cm.

In one aspect, the micro-fabricated device is a prepared by a method comprising soft-lithography of a plasma-treated micro-textured master or a textured balloon with grooved surface features to impose contact guidance cues during chamber creation.

In one aspect, the plurality of cells have been removed from the micro-textured surface.

In one aspect, the aligned cardiomyocytes or population of cells are ventricular cardiomyocytes. In one aspect, the aligned ventricular cardiomyocytes are anisotropic.

In one aspect, the aligned cells or population of cells have at least one of a transverse conduction velocity of from about 2 to about 4 cm/s, or from about 2.5 to about 3.5 cm/s at 1 Hz or a longitudinal conduction velocity of from about 3 to about 8 cm/s at 1 Hz, or from about 2 to about 7 cm/s at 1 Hz. In one aspect, the the aligned cells or population of cells have an average anisotropy ratio (AR) of from about 0.5 to 1.5.

The plasma used here, in one aspect, is one or more of oxygen plasma, helium plasma or hydrogen plasma.

The source cells that are used in the methods include stem cells, e.g., embryonic stem cells or induced pluripotent stem cells (iPSCs). In one aspect, the stem cells are human embryonic stem cells (hESCs). In a further aspect, the hESCs are from a stem cell line such as HES2 stem cell (NIH cod ES02). The cells are cultured on the textured surface without the use of feeder cells e.g., feeder free and passaged when the culture reaches greater than 65%, or alternatively greater than 70%, or alternatively greater than 75%, or alternatively greater than 80%, or alternatively greater than 85%, or alternatively greater than 90%, confluence. The culture medium is changed at least every two days, or alternatively at least every day (a day comprising from about 22 to 26 hours and thus, every day intends every 22 to 26 hours, or alternatively at least about every 24 hours). The cells are then dispersed into smaller cultures (from about 50 to 100 cells each), and cultured in differentiation media that supports differentiation into cardiomyocytes. A non-limiting example of such is StemPro34 (as described herein) and in one aspect, supplemented as described herein. Differentiation medium is replaced every two days, or alternatively at least every day (a day comprising from about 22 to 26 hours and thus, every day intends every 22 to 2.6 hours, or alternatively at least about every 2.4 hours) up to about day 18 to 20, as calculated from initial culturing or from use of the differentiation medium. The differentiated cells are then dissociated and plated on control or aligned extracellular matrix (ECM) coated polyethylene substrates for at least 5 days, or alternatively at least 6 days, or alternatively at least 7 days, or alternatively at least 8 days, or alternatively at least 9 days, to establish intercellular electrical junctions.

In one aspect, the surface is treated with an extracellular matrix (ECM) prior to culturing and differentiating the cells. Several ECMs are known in the art, e.g., Matrigel is the trade name for a gelatinous protein mixture secreted by Engelbreth-Holm-Swarm (EHS) mouse sarcoma cells and marketed by BD Biosciences and by Trevigen Inc under the name Cultrex BME. This mixture resembles the complex extracellular environment found in many tissues and is used by cell biologists as a substrate for cell culture. A laboratory procedure is to dispense small volumes of chilled (4° C.) Matrigel onto plastic tissue culture labware. When incubated at 37° C. (body temperature) the Matrigel proteins self-assemble producing a thin film that covers the surface of the labware. An alternative is supplied by AMSEBIO under the tradename PathClear® Grade Basement Membrane Extract. Sigma-Aldrich also supplies an ECM gel.

Any appropriate method can be used to dissociate the cells, e.g., by lowered (below 32° C.) the temperature. Upon temperature actuation, the cells are released together with intact membrane proteins. See, for example, International Publ. No PCT/US2010/046670, incorporated herein by reference.

In one aspect, the cells are stem cells or cells derived or differentiated from a stem cell such as a stem cell derived cardiomyocytes or embryonic stem cells, pluripotent cells, iPSCs or embryoid bodies. Also provided therefore, is a plurality of derived cells, such as cardiomyocytes, such as in a monolayer, prepared by aligning the cells on a textured surface by culturing an isolated cell that can differentiate into a cardiomyocyte. In one aspect, the cardiomyocytes comprise or have the functionality of possessing an action potential. Such cardiomyocytes can be measured for their action potentials and conduction properties which are useful in characterizing the cardiomyocytes or the stem cells from which they are derived.

Still further provided are a monolayer of cells, such as cardiomyocytes, prepared by any methods described herein on the substrate or alternatively, removed therefrom. The cells can be substantially homogeneous or heterogeneous. A preferred heterogeneous population is of the group of the hESC-VCMs:fibroblasts of about 1:0; 1:1; 2:1; or 1:2.

The disclosed methods create well-controlled multi-scale (nano- to micro-) grooves which are effective to induce the alignment of human embryonic stem cells (hESCs) as well as hESC-derived stem cells, cardiomyocytes (hESC-CM) for improved physiological functionality.

The methods are not limited to any particular method or composition of the substrate to grow the cells. In addition, optimized or particular parameters can be translated into 3D systems (e.g., cell and matrix alignments to make anisotropic organoids or "mini heart chambers") for examining their electro-mechanical function, compared to baseline isotropic organoids with random structural alignment. Control of organoid shape and boundary conditions can yield random (isotropic) and aligned (anisotropic) cell orientations, If finer control of the level of anisotropy is necessary for optimal hESC-VCM maturation, it may be possible to regulate alignment of cells and collagen matrix using newly developed textured balloons with grooved surface features to impose contact guidance cues during chamber creation. Two and three-dimensional structures can be subjected to global ischemia (by culturing in a 5% $O_2$ environment) or other experimental conditions (to mimic physiological or pathophysiological conditions) followed by examining the resultant functional changes. Particular attention can be paid to their change in susceptibility to arrhythmias.

By way of example, pre-stressed polyethylene (PE), is shrunk uniaxially to create self-similar aligned grooves or "wrinkles."

The material can be pre-stressed prior to the plasma treatment. When the material is pre-stressed, the shrinking can be achieved by removing the stress. In another aspect, the shrinking is achieved by heating the material, whether the material has been pre-stressed. In a further aspect, the shrinking is performed after plasma treatment.

In some aspects, the shrinking is uniaxial or biaxial. In some aspects, the material is shrunk by at least 60% or more.

Thermoplastic materials suitable for practicing the present technology include, without limitation, a high molecular weight polymer, polyolefin, polyethylene, acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), polyacrylonitrile (PAN or Acrylonitrile), polyamide (PA or Nylon), polyarnide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PEI), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC) or spectralon. In one aspect, the thermoplastic material comprises polyolefin. In another aspect, the thermoplastic material comprises polyethylene.

The plasma treated thermoplastic and shrunk material provides a "master" mold which is then used to provide micro-textured cell culture plates, surfaces or devices to culture the cells.

The textured micro-surface have substantially aligned wrinkles or grooves an intergrove distance and independently of groove depth of about 0.1, or 1.0 or 10.0 mm (and ranges in between, e.g., from about 0.1 to about 10.0 mm, or about 0.5 to about 5.0, or about 0.7 to about 1.3; or about 0.1 to about 1.0; or about 1.0 to about 10.0 mm, and increments of 0.1 therebetween. Substrate stiffness is from about 0.5 to about 150 kPa, or about 1.0 to about 100 kPa, or about 50 to about 100 kPa; or about 1.0 to about 10 kPa; or about 1.0 kPa, or about 10 kPa or about 100 kPa.

The methods and compositions can be used to screen candidate agents for their ability to modulate and effect stem cell differentiation by contacting a candidate agent with the cells aligned on the substrate and monitoring the effect (if any) of the agent on the cells. Kits to grow cells and perform the screen are provided herein.

DETAILED DESCRIPTION OF THE DISCLOSURE

Definitions

Figure 1:
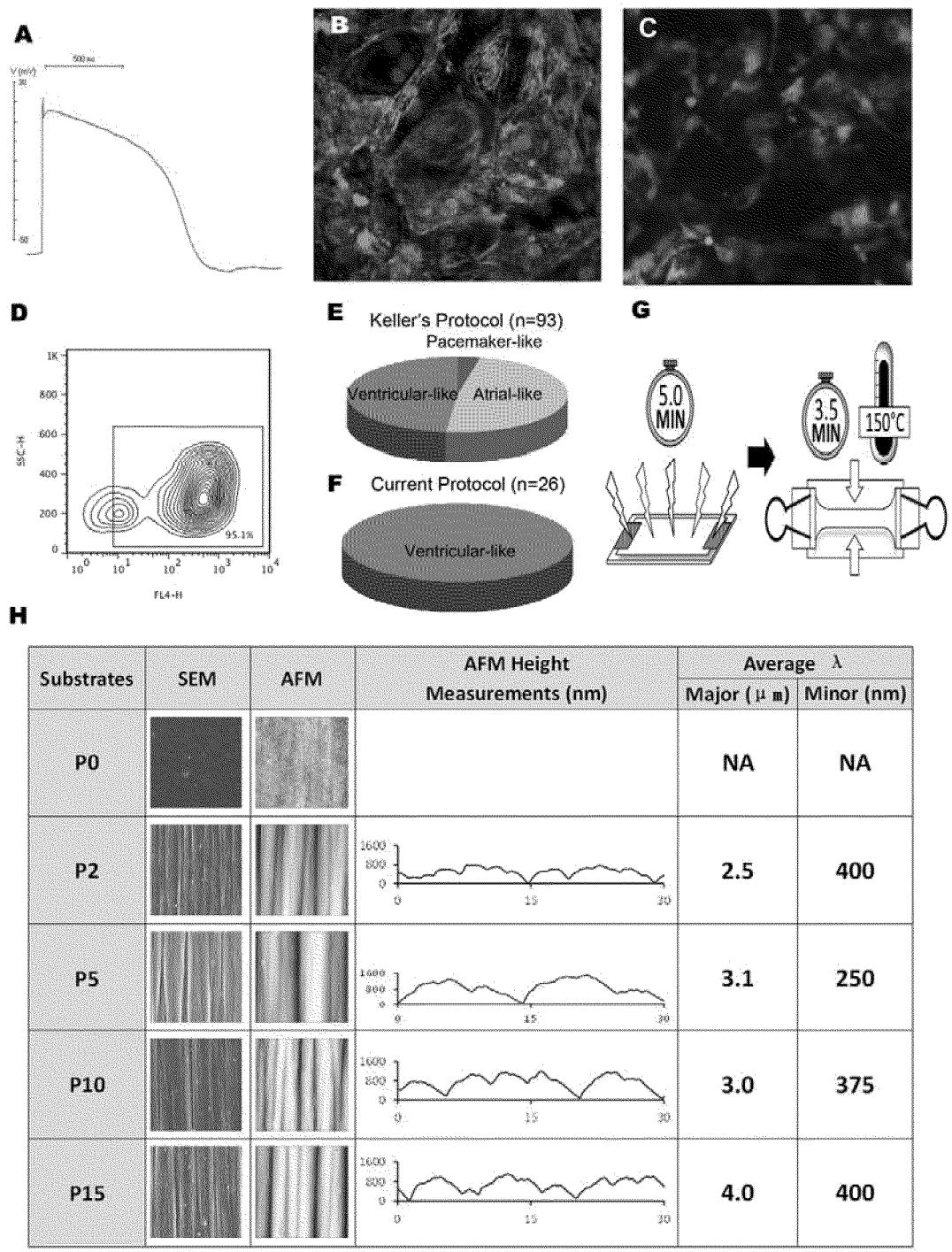
FIG. 1A-H show the ventricular specification of hESCs and characterization of wrinkled substrates. A) Representative AP tracing indicates a ventricular phenotype. B) Positive staining by MLC2v and C) GFP expression after transduction by LY-MLC2v-GFP. D) Flow cytometry indicates that ~95% of the derivatives were TnT-positive. E and F) Pie charts showing the percentage distribution of ventricular-, atrial- and pacemaker-like AP phenotypes. G) For shrink film fabrication, pre-stressed polyethylene film is treated with oxygen plasma for e.g. 5 minutes. The plasma treated film is then constrained on the opposite sides and shrunk at 150° C. for 3.5 minutes. H) SEM (1,000×) and AFM images (30×30 μm$^2$) of control and wrinkled substrates plasma treated for 0, 2, 5, 10, and 15 min (P0-P15, respectively). Averaged wrinkle heights and wavelengths are also given.

As used herein, certain terms may have the following defined meanings.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps for preparing the intended device. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least,"

"greater than," "less than," and the like include the number recited and refer to ranges which can be subsequently broken down into subranges as discussed above.

A "thermoplastic material" is intended to mean a plastic material which shrinks upon heating or upon release of pre-stress such as a stress created by stretching. In one aspect, the thermoplastic materials are those which shrink uniformly without distortion. The shrinking can be either bi-axially (isotropic) or uniaxial (anisotropic). Suitable thermoplastic materials for inclusion in the methods of this invention include, for example, polyolefin, polyethylene, high molecular weight polymers such as acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), polyacrylonitrile (PAN or Actylonitrile), polyamide (PA or Nylon), polyamideimide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyalkanoates (PHAs), polyketone (PK), polyester polyethylene (PE), polyetheretherketone (PEEK), polyetherimide (PEI), polyethersulfone (PES), polysulfone polyethylenechlorinates (PEC), polyimide (PI), polylactic acid (PLA), polymethylpentene (PMP), polyphenylene oxide (PPO), polyphenylene sulfide (PPS), polyphthalainide (PPA), polypropylene (PP), polystyrene (PS), polysulfone (PSU), polyvinyl chloride (PVC), polyvinylidene chloride (PVDC) and spectralon.

In some aspects, the thermoplastic material encompasses polyolefin. A polyolefin is a polymer produced from a simple olefin (also called an alkene) as a monomer. For example, polyethylene is the polyolefin produced by polymerizing the olefin ethylene. Polypropylene is another common polyolefin which is made from the olefin propylene.

In some aspects, the thermoplastic material encompasses shape memory polymers (SMPs). SMPs are polymeric smart materials that have the ability to return from a deformed state (temporary shape) to their original (permanent) shape induced by an external stimulus (trigger), such as temperature change.

Commercially available thermoplastic materials include, without limitation, "Shrinky-Dink" and porous films such as Solupore®. Shrinky-Dink is a commercial thermoplastic which is used a children's toy. Solupore® is available from Lydall, Inc. of Manchester, Conn.

"Soft-lithography" is intended to refer to a technique commonly known in the art. Soft-lithography uses a patterning device, such as a stamp, a mold or mask, having a transfer surface comprising a well-defined pattern in conjunction with a receptive or conformable material to receive the transferred pattern. Microsized and nanosized structures are formed by material processing involving conformal contact on a molecular scale between the substrate and the transfer surface of the patterning device.

The term "receptive material" is intended to refer to a material which is capable of receiving a transferred pattern. In certain embodiments, the receptive material is a conformable material such as those typically used in soft lithography comprise of elastomeric materials, such as polydimethylsiloxane (PDMS). The thermoplastic receptive material, or thermoplastic material, is also a receptive material as it can be etched, for example.

"Imprint lithography" is intended to refer to a technique commonly known in the art. "Imprint lithography" typically refers to a three-dimensional patterning method which utilizes a patterning device, such as a stamp, a mold or mask.

A "mold" is intended to mean an imprint lithographic mold.

A clone is a line of cells that is genetically identical to the originating cell; in this case, a stem cell. "Clonal proliferation" refers to the growth of a population of cells by the continuous division of single cells into two identical daughter cells and/or population of identical cells.

The term "propagate" means to grow or alter the phenotype of a cell or population of cells, The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of an embryoid body. In some aspects "growing" also infers differentiation of a pluripotent or stem cell into a cell of a defined lineage.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

As used herein, the "lineage" of a cell defines the heredity of the cell, i.e. its predecessors and progeny. The lineage of a cell places the cell within a hereditary scheme of development and differentiation.

"Embryoid bodies or EBs" are three-dimensional (3-D) aggregates of embryonic stem cells formed during culture that facilitate subsequent differentiation. When grown in suspension culture, ES cells form small aggregates of cells surrounded by an outer layer of visceral endoderm, Upon growth and differentiation, EBs develop into cystic embryoid bodies with fluid-filled cavities and an inner layer of ectoderm-like cells.

A derivative of a cell or population of cells is a daughter cell of the isolated cell or population of cells. Derivatives include the expanded clonal cells or differentiated cells cultured and propagated from an isolated stem cell or population of stem cells. Derivatives also include already derived stem cells or population of stem cells, such as, embryoid bodies from an embryonic stem cell.

"Differentiation" describes the process whereby an unspecialized cell acquires the features of a specialized cell such as a heart, liver, or muscle cell, "Directed differentiation" refers to the manipulation of stern cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell, As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype, Phenotype can be determined by a pre-selected cell surface marker or other marker, e.g. myosin or actin or the expression of a gene or protein, e.g. a calcium handling protein, a t-tubule protein or alternatively, a calcium pump protein. In another aspects, the substantially homogenous population have a decreased (e.g., less than about 95%, or alternatively less than about 90%, or alternatively less than about 80%, or alternatively less than about 75%, or alternatively less than about 70%, or alternatively less than about 65%, or alternatively less than about 60%, or alternatively less than about 55%, or alternatively less than about 50%) of the normal level of expression than the wild-type counterpart cell or tissue.

Methods for Preparing the Surfaces for Growing the Cells

The methods for differentiating the cells as described herein use a textured surface that is biocompatible, comprising, or alternatively consisting essentially of, or yet further consisting of, shrinking a thermoplastic material, thereby preparing a textured surface on the material, wherein the material has been treated by a plasma before or after the shrinking. Such methods are known in the art and described, for example in International Application Nos. PCT/US2010/046670; PCT/US2010/034612 and PCT/US2010/034613. Examples of thermoplastic materials are disclosed herein.

Plasmas can be prepared with methods known in the art and can vary depending on availability of sources. In one embodiment, the plasma is one or more of oxygen plasma, helium plasma, or hydrogen plasma. In a particular embodiment, the plasma is oxygen plasma.

The duration of plasma treatment can vary and depend on the desired scale of the texture and/or the thermoplastic material, for instance. In one aspect, the plasma treatment takes more than about 10 seconds, or alternatively more than about 20 seconds, about 30 seconds, about 1 minute, about 2 minutes, about 3 minutes, about 4 minutes, about 5 minutes, about 7 minutes, about 10 minutes, about 15 minutes, about 20 minutes, about 25 minutes, or about 30 minutes. In another aspect, the plasma treatment takes less than about 60 minutes, or alternatively less than about 45 minutes, about 30 minutes, about 25 minutes, about 20 minutes, about 15 minutes, about 10 minutes, about 7 minutes, about 5 minutes, about 4 minutes, about 3 minutes, about 2 minutes, about 1 minute, about 30 seconds, or about 20 seconds. In another aspect, the plasma treatment is for an interval between about 0.5 minutes up to 30 minutes, or a 0,5 minute interval therebetween (e.g., 1.5 minute, or 2.0 minute, or 2.5 minute). In some aspects, the treatment is carried out in a closed chamber. In some aspects, the treatment is carried out in a handheld corona discharger.

The thermoplastic material can be pre-stressed prior or after to the plasma treatment. in such a case, the shrinking can be achieved by removing the stress. Such a stress can simply be stretching, either uniaxially or biaxially.

Alternatively, the shrinking can be achieved by heating the material. In one aspect, the plasma treated film is constrained on the opposite sides and shrunk at an appropriate temperature (e.g., about 150 degrees Celcius) for about 2 minutes, or alternatively about 3 minutes, or alternatively about 3.5 minutes, or alternatively about 4.0 minutes, or alternatively about 4.5 minutes, or alternatively about 6 minutes, or more. Depending on the material and desired scale of texture, the temperature can vary. In one aspect, the heating is at least about 100° C., or at least about 125° C., or at least about 150° C., or at least about 175° C., or at least about 200° C. In one aspect, the heating is from about 100 to about 200° C., or alternatively from about 125 to about 175° C., or about 150° C.

Shrinking of the material can be uniaxial or biaxial. When the material is shrunk uniaxially, the texture may be one dimensional. When the material is shrunk biaxially, the texture may be two dimensional.

In some embodiments, the material is shrunk, uniaxially or biaxially, by at least about 60%, or alternatively at least about 70%, about 75%, about 80%, about 85%, about 90%, about 91%, about 92%, about 93%, about 94%, about 95%, about 96%, about 97%, about 98%, or about 99% from its original size.

After the polymeric material is treated and shrunk, it is used as a mold for a second polymeric form conforming material. The term "form conforming material" is intended to refer to a material which is capable of receiving a transferred pattern which may also be referred to as a "receptive material". In certain embodiments, the material includes such as those typically used in soft lithography and therefore comprise elastomeric materials, such as polydimethylsiloxane (PDMS), gelatin, agarose, polyethylene glycol, cellulose nitrate, polyacrylamide or chitosan.

Soft or imprint lithography can used to create the device from the mold using the form-conforming material. The molding or the lithography comprises, or alternatively consists essentially of, or yet further consists of a process such as soft lithography or imprint lithography. These methods are known in the art and disclosed in US Patent Publication Nos.: 2012/0064627; 2011/0122406; and 2012/0129209.

Examples of form conforming materials include without limitation a material comprising one or more of polydimethylsiloxane (PDMS), gelatin, agrose, polyethylene glycol, cellulose nitrate, polyacrylamide, and chitosan.

In one aspect, the lithography uses a thermoplastic material.

In one aspect, the material used in lithography, such as PDMS, is poured onto the plasma treated surface, which serves as the mold, as in typical soft lithography, and cured at 110° Celsius for 10 minutes. The cured PDMS device is then peeled of the mold and bonded using a hand-held corona discharger (Haubert K., et al. (2006) Lab Chip Technical Note 6: 1548-1549). The whole process from device design conception to working device can be completed within minutes.

In one aspect, the surface is treated with an extracellular matrix (ECM) prior to culturing and differentiating the cells. Several ECMs are known in the art, e.g., Matrigel is the trade name for a gelatinous protein mixture secreted by Engelbreth-Holm-Swarm (EHS) mouse sarcoma cells and marketed by BD Biosciences and by Trevigen Inc under the name Cultrex BME. This mixture resembles the complex extracellular environment found in many tissues and is used by cell biologists as a substrate for cell culture. A common laboratory procedure is to dispense small volumes of chilled (4° C.) Matrigel onto plastic tissue culture labware. When incubated at 37° C. (body temperature) the Matrigel proteins self-assemble producing a thin film that covers the surface of the labware. An alternative is supplied by AMSBIO under the tradename PathClear® Grade Basement Membrane Extract. Sigma-Aldrich also supplies an ECM gel.

The textured micro-surface have substantially aligned wrinkles or grooves an intergrove distance and independently of groove depth of about 0.1, or 1.0 or 10.0 mm (and ranges in between, e.g., from about 0.1 to about 10.0 mm, or about 0.5 to about 5.0, or about 0.7 to about 1.3; or about 0.1 to about 1.0; or about 1.0 to about 10.0 mm, and increments of 0.1 therebetween. Substrate stiffness is from about 0.5 to about 150 kPa, or about 1.0 to about 100 kPa, or about 50 to about 100 kPa; or about 1.0 to about 10 kPa; or about 1.0 kPa, or about 10 kPa or about 100 kPa.

Aligning Stem Cells or Cardiomyocytes and Aligned Cells

The textured surfaces prepared by the present technology can be used to align cells, in particular stem cell and used to differentiate embryonic stem cells. In one aspect, the cells are human embryonic stem cells, iPSCs or stem cell derived cardiomyocytes. Also provided, therefore, are a plurality of cardiomyocytes, such as a monolayer, prepared by aligning the cells on a textured surface. In one aspect, the plurality of cells are substantially homogenous.

The stem cells can be cultured under feeder-free conditions and passaged when the culture reached ~80% confluence, for instance. Stem cell culture medium is changed daily. For ventricular specification, stem cell colonies can be dissociated by dispase (at e.g., 1 mg/ml) into smaller clusters (50-100 cells) followed by culturing in differentiation media. Differentiation media, for instance, can include about 50 μg/ml ascorbic acid and about 2 mM GlutaMAX-I supplemented with cytokines and Wnt inhibitor as follows: day 1 BMP4 (1 ng/ml) and blebbistatin (5 μM); days 2-4.5 human recombinant BMP4 (10 ng/ml) and human recombinant Activin-A (5 ng/ml); days 4.5-7, IWR-1 (1 μM).

Differentiation medium can be replenished daily until day 18-20, at which time aligned cells are dissociated and plated on control or the textured surface for 7 days to allow establishment of intercellular electrical junctions before electrical recordings.

Methods to grow the cells are described herein and use them for drug screening are described herein.

Kits

This disclosure also provides a kit to culture aligned cells on a micro-textured surface, comprising a thermoplastic material, form-containing material, associated material such as plasma, cell culture media and instructions for making the micro-textured surface, culturing and differentiating cells, and removing the cells from the surface and as provided herein.

EXPERIMENTAL EXAMPLES

Example 1

Engineered Anisotropy of Human Embryonic Stem Cell-Derived Ventricular Cardiomyocytes by Physical Alignment for Enhanced Safety Against Arrhythmias This example demonstrates that multi-scale topography enables physical alignment of hESC-VCMs thereby reproducing functional anisotropy. Aligned anisotropic hESC-VCMs are less susceptible to arrhythmias, and may lead to future transplantable prototypes with improved efficacy and safety as well as more accurate models for arrhythmogenicity screening.

Materials and Methods

HESC Culture and Ventricular Specification.

Electrophysiological heterogeneity is a known contributing factor to sustained reentry and arrhythmias. To avoid dispersion of refractoriness due to mixed chamber-specific subtypes from in vitro cardiac differentiation, this example employed a modified ventricular specification protocol (Karakikes et al., Stem Cells Transl Med., 3(1):18-31, 2014)).

The revised protocol generates >95% hESC-VCMs as gauged by AP recording, troponin T (TnT)-positive immunostaining, and GFP expression under transcriptional control of the MLC2v-promoter (FIG. 1A-D). In brief, undifferentiated hESCs (HES2 line, NIH code ES02) were cultured under feeder-free conditions and passaged when the culture reached ~80% confluence. Stem cell culture medium (mTeSR1, Stem Cell Technologies, Vancouver, BC, Canada) was changed daily. For ventricular specification, hESC colonies were dissociated by dispase (1 mg/ml) into smaller clusters (50-100 cells) followed by culturing in differentiation media (StemPro34 50 μg/ml ascorbic acid and 2 mM GlutaMAX-I; Invitrogen, Carlsbad, Calif.) supplemented with cytokines and Wnt inhibitor as follows: day 1 BMP4 (1 ng/ml) and blebbistatin (5 μM); days 2-4.5 human recombinant BMP4 (10 ng/ml) and human recombinant Activin-A (5 ng/ml); days 4.5-7, IWR-1 (1 μM).

Differentiation medium was replenished daily until day 18-20, at which time hESC-VCMs were dissociated and plated on control or aligned Matrigel coated polyethylene substrates for 7 days to allow establishment of intercellular electrical junctions before electrical recordings. Only intact preparations without structural or geometric defects were used tier experiments.

Fabrication and Characterization of Wrinkle Substrates

The fabrication method has been previously described (Chen et al., Adv Mater. 2011; 23(48):5785-91). Briefly, pre-stressed polyethylene shrink film was treated with oxygen plasma (Plasma Prep II, SPI Supplies) for 2, 5, 10, or 15 minutes to generate P2, P5, P10 and P15 substrates. The plasma treated film was then constrained on opposite sides, and was shrunk at 150° C. for 3 minutes to create microwrinkled masters, which were then replicated using soft lithography with PDMS to yield substrates for inducing cell alignment (FIG. 1G).

Both scanning electron microscopy (SEM) and atomic force microscopy (AFM) were performed to characterize the wrinkles (FIG. 1H). For SEM, wrinkles were sputter coated (Polaron SC7620) with 4 nm gold, and images were obtained at 1,000× magnification (FEI Quanta 3D FEG), Wavelengths of wrinkles were obtained by analyzing the SEM images using an in-house MATLAB (MathWorks Inc., Natick, Mass., USA) fast Fourier transform code. AFM was performed on a MFP-3D inverted optical microscope (Asylum Research, Santa Barbara, Calif.). The topographic of images were taken in tapping mode with a tip resonant frequency of about 75 kHz and force constant of 3 N/m. Data acquisition and analysis were performed with IGOR Pro 6.0 (Wavemetrics, Portland, Oreg.).

Optical Mapping

HESC-VCM preparations were loaded with 4 μM di-4-ANEPPS (Invitrogen, USA) for 20 min at room temperature in Tyrode's solution, consisting of (mM) 140 NaCl, 5 KCl, 1 MgCl2, 1 CaCl2, 10 glucose, and 10 HEPES at pH 7.4, then washed twice before fluorescence imaging using a halogen light filtered by a 515±35 nm band-pass excitation filter and a 590 nm high-pass emission filter. High-resolution optical mapping of AP and conduction properties was performed using a MiCam Ultima (SciMedia, Calif., USA) with a 1X objective and a 1X condensing lens to yield a 10×10 mm² field of view. A custom heat plate was introduced to maintain the perfused Tyrode's solution at 37° C. Data were collected at a sampling rate of 200 Hz and analyzed using BV_Ana software (SciMedia). Isoproterenol (Sigma-Aldrich, N.Y., USA) was applied by perfusion at the concentrations indicated.

Electrophysiology

Electrophysiological protocols were generated using a programmable stimulator (Master8, AMPI, Israel) with the stimuli delivered via a unipolar point-stimulation electrode (1.5× threshold, 10 ms duration) placed perpendicular to the preparation surface. Steady-state pacing was initiated at a rate of 0.5 Hz, except in the presence of isoproterenol when 1.5-2.0 Hz frequency was imposed to overdrive the positive chronotropic effect on intrinsic rhythm. The frequency was increased every minute in 0.1-Hz increments with a 5-sec pause.

Mapping was performed during the last 5-10 seconds of each frequency. Pacing was aborted if monolayers failed to capture stimuli at 1:1 ratio. Programmed electrical stimulation, Standard (S1-S2) programmed electrical stimulation (PES) protocol was introduced to study the electrical restitution curve (ERC) of hESC-VCMs. A premature extrastimulus (S2) was delivered after a train of eight S1 stimuli at a basic cycle length (BCL) of 650 ms. S1-S2 interval was initiated at 600 ms and consecutively shortened in steps of 20 ms until capture has failed. S1-S2 interval was then increased by 18 ms afterward, followed by 2-ms increments until the effective refractory period (ERP), defined as the maximum S1-S2 interval that failed to lead to AP propagation, was achieved. There was a pause of 10 s after each S2. The entire stimulation protocol was performed within 30 minutes after di-4-ANEPPS staining.

Standard parameters such as action potential duration (APD) and conduction velocities were analyzed as previously described (Xue et al., Circulation. 2005; 111(1):11-20; Tse et at., Circulation. 2006; 114(10):1000-11). APD restitution (APDR) curve was generated by plotting APD90 of S2 against the foregoing diastolic interval (DI), which is determined by the last APD90 of S1 subtracted from the S1-S2 interval. The restitution curve was fitted with the following mono-exponential equation:

$$y(APD_{90}) = y_0 + A_1(1 - e^{(-DI/\gamma_1)})$$

where $A_1$ and $\gamma_1$ are parameters of the fit. The maximum slope of ERC ($Slope_{max}$) is a function of the minimum DI ($DI_{min}$) as defined in the following equation:

$$Slope_{max} = \frac{A_1}{\gamma_1} \text{Exp}\left(\frac{-DI_{min}}{\gamma_1}\right)$$

Data were presented as mean value±SD. Student's t test and ANOVA test were employed with P<0.05 considered statistically significant.

Results

Electrophysiology of 2D preparations of hESC-VCMs.

Figure 2:
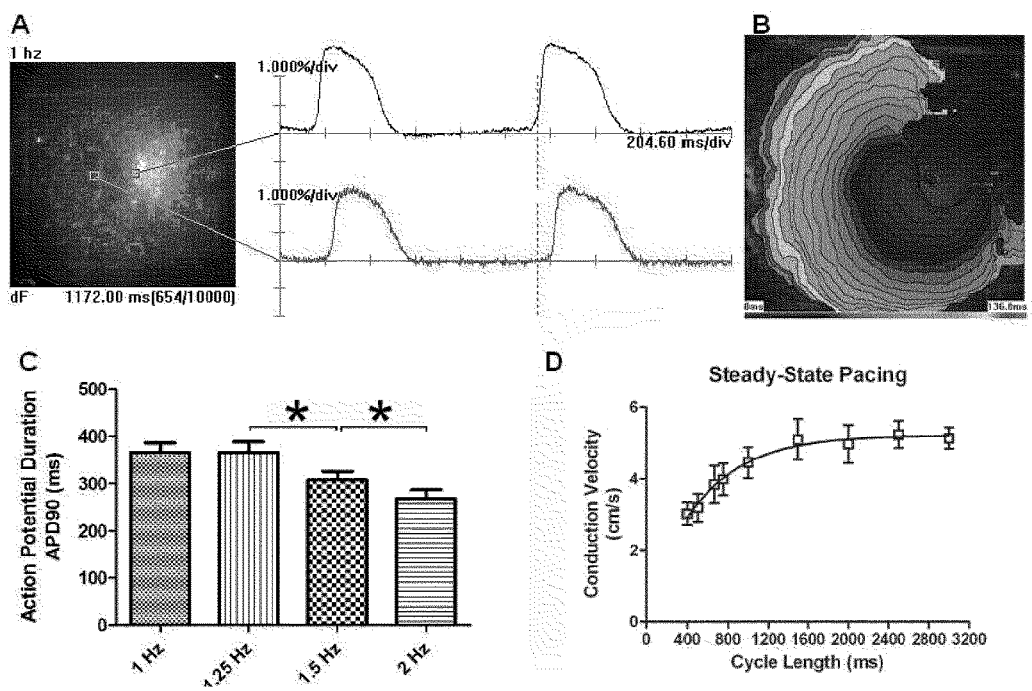
FIG. 2A-D show action potential and conduction properties of hESC-VCMs on unaligned control substrate. A) Representative APs at two different sites during 1 Hz pacing. B) A typical isochrone map with 12 ms intervals shows a circular spreading pattern of optically mapped transmembrane potentials upon point stimulation (white circle) with no preferential directionality. C) Rate adaptation of APs. D) Conduction velocities dependency on pacing cycle length. Data were collected from 60 sites of 6 samples, *p<0.01.

To study conduction and other multi-cellular properties, single hESC-VCMs were allowed to reaggregate and form 2-dimensional preparations (monolayers) fur high-resolution optical mapping. FIG. 2A shows APs optically mapped on a typical 2-D preparation of hESC-VCMs upon point stimulations at 1 Hz. Representative AP tracings mapped from two sites distal to the unipolar pacing electrode (white circle) showed that their morphologies resembled each other, as anticipated from the homogenous population, but a systematic sequential time delay (185 ms/cm) was consistently observed.

FIG. 2B shows the isochronal conduction contour map (with intervals of 12 ms) of the same preparation, demonstrating a centrifugal propagation of the depolarizing wavefront (dF/dt) from the electrode, with an average conduction velocity of 5.0±1.4 cm/s (n=16). However, the spread was circular and isotropic; measurements of arbitrarily chosen transverse (T-) and longitudinal (L-) conduction velocities (CV) consistently yielded an anisotropy ratio (AR) of 11.0±0.2 (n=16). At successively faster frequencies of steady-state pacing, $APD_{90}$ decreases (374±16.8 ms, 362±24.2 ms, 337±39.3 ms and 266±17.0 ms at 1.0 Hz, 1.25 Hz, 1.5 Hz and 2 Hz, respectively; FIG. 2C) indicating rate adaptation.

Similarly, rate-dependence of CV on the cycle length (i.e. reciprocal of rate or frequency) was observed (FIG. 2D). The wavelength (WL), calculated as the product of CV and APD, was 1.8±0.5 cm at 1.0 Hz.

Physical Alignment of hESC-VCMs Leads to Anisotropic Properties

Figure 3:
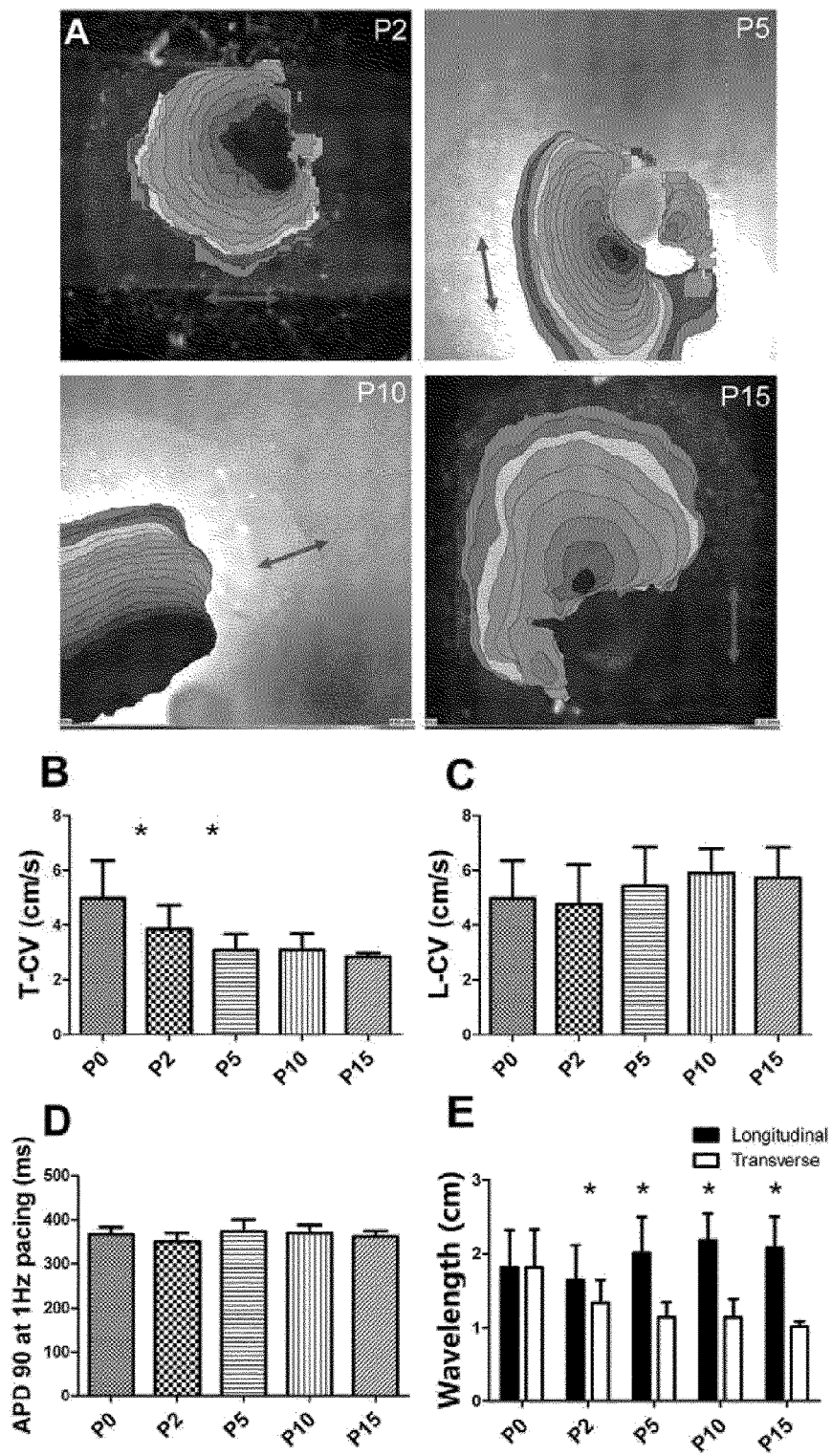
FIG. 3A-E show effects of cell alignment. A) Typical isochrone maps of various aligned substrates (P2, P5, P110 and P15) with 16-ms intervals. Double-end arrows indicate the longitudinal direction of the major axis of the wrinkled substrate. The products of transverse (B) or longitudinal (C) conduction velocities and APD90 (D) of different substrates give rise to the transverse and longitudinal wavelength (E). * p<0.01, longitudinal vs. transverse.

This example next examined the functional consequences of physically aligned hESC-VCMs. Unlike the circular conduction pattern of control preparations, AP propagation of P5-aligned preparations displayed an elliptical shape with distinct transverse (3.1±0.6 cm/s, n=14) and longitudinal (5.4±1.4 cm/s, n=14) conduction velocities at 1 Hz, giving rise to an AR of 1.8 (FIG. 3A-C). This alignment-induced AR was comparable to that of native ventricles.

Figure 4:
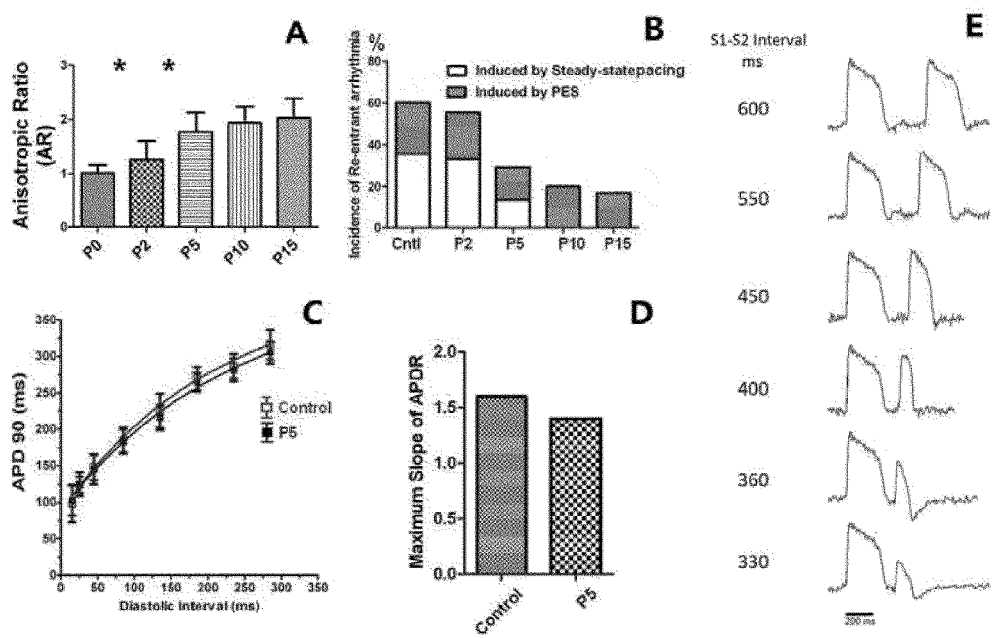
FIG. 4A-E show that alignment reproduces anisotropy and reduces the incidence of reentrant arrhythmias. A) Anisotropy ratios of tested substrates. B) Incidence of spontaneous (open) and PES-induced (solid) reentrant arrhythmias, C) Representative MAPs. D) AP duration restitution curves and E) maximum slopes of APDR of control and P5 hESC-VCMs. *, p<0.01.

Therefore, subsequent experiments were focused on P5 preparations, Similar oval anisotropic patterns were observed with P2-, P10- and P15-aligned preparations. AR depended on groove geometry. This example observed a plateau in this effect at P10 and P15 (FIG. 4A). Also, no statistical differences were observed in $APD_{90}$ among control (P0) and all the aligned preparations (i.e. P2, P5 and P10) at any of the frequencies tested (FIG. 3D). Compared to control, WL propagating along the transverse direction on P5-, P10- and P15-aligned substrates significantly decreased (p<0.05) (FIG. 3E).

Figure 5:
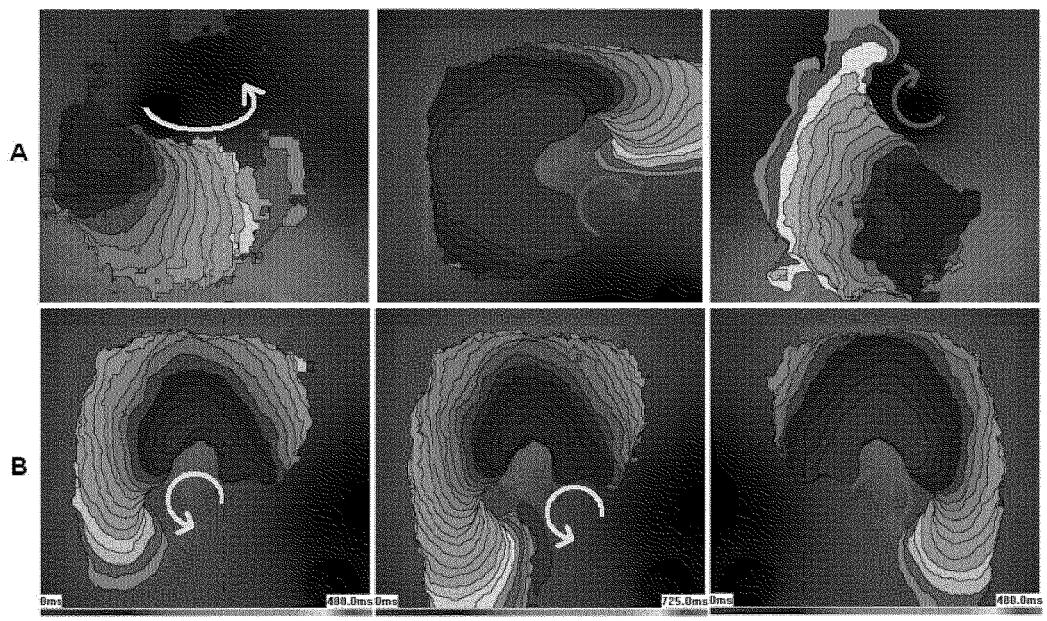
FIG. 5A-B include images showing reentrant arrhythmias. Representative isochronal maps of sustained functional reentries in the form of spiral waves that spontaneously occurred A) during steady-state pacing, or B) induced by PES, Chirality is shown by red (+, clockwise) and yellow (−, counter-clockwise) arrows.

Aligned Anisotropic hESC-VCMs Displayed Reduced Incidence of Reentrant Arrhythmias During steady-state pacing at 1.5 to 2.0 Hz, 6 of 16 control preparations (i.e. 37.5%) displayed spontaneous sustained functional reentry (FIG. 4B, open bar) in the form of spiral waves (FIG. 5A), unitary or elementary events of fibrillation, with a rotation duration of 938±184 ms (n=10) and a rate of 1.1±0.2 Hz. Preparations that did not display spontaneous reentry arrhythmias were further tested tier their inducibility for arrhythmias using the standard (S1-S2) PES protocol (FIG. 5B). Of the remaining 10 controls, functional reentry could be successfully induced in 4 (i.e. 25% of total; FIG. 4B, solid bar). Therefore, 62.5% of all control preparations were susceptible to spontaneous or inducible reentry arrhythmias. Of the 5 control preparations that did not exhibit sustained reentry, the AP wavefront broke into multiple (2 or more) separate wavefronts along its propagation path but without becoming a sustained spiral wave.

At 2.0 to 2.5 Hz, cell alignment substantially reduced (P2=33.3%, 9 preparations in total; P5=21.4%, 14 preparations in total) or eliminated (P10=0%, 6 preparations in total; P15=0%, 6 preparations in total) the incidence of spontaneous reentry; aligned preparations were also less susceptible to PES-induced arrhythmias (P2=22.2%, P5=21,4%, P10=16.7%, P15=16.7%) (FIG. 4B). Therefore, the total incidence of spontaneous and induced reentrant arrhythmias was substantially reduced.

Representative maps are shown in FIG. 5A-B. Rotation duration and rate of spontaneous or induced spiral waves did not appear to depend on the extent of alignment (Table 1), suggesting that only the thresholds to sustained reentry were altered. Different chiralities (clockwise (+) counterclockwise (−)=6/4, 3/2, 1/3, 1/0 and 0/1 for control, P2, P5, P10 and P15, respectively) were observed in spiral waves. However, there was not an obvious correlation between the rotation and alignment directions.

TABLE 1

Rotation rates of reentrant arrhythmias of tested substrates

| Substrate | Rotation rate (Hz) |
|---|---|
| Control | 1.1 ± 0.18 |
| P2 | 1.2 ± 0.15 |
| P5 | 1.2 ± 0.21 |
| P10 | 1.1 ± 0.16 |
| P15 | 1.1 ± 0.20 |

FIG. 4C depicts a representative example of monophasic action potential (MAP) of control monolayer recorded at a basic cycle length (BCL) of 650 ms with progressively shortened S1-S2 coupling intervals, Upon stimulation, a typical MAP began with a rapid. upstroke, immediately followed by a quick repolarization by about 5-10% of its maximum amplitude followed by a 'plateau' phase (shoulder) that lasted 200-250 ms before returning to the resting membrane potential (RMP). As the S1-S2 coupling interval decreased from 550 ms to 330 ms, the APD90 and amplitude of MAP decreased (from 305 ms to 108 ms) and became attenuated. The amplitude of MAP measured at BCL was 2.4-fold of that at 330 ms S1-S2 interval. The effective refractory period (ERP) of 258±38 ms was reached when S1-S2 further shortened.

FIG. 4D shows a representative APD restitution curve of control where APD90s (averaged from 10 sites of each of 4 independent preparations) were plotted against the diastolic interval (DI, difference between the last APD90 of S1 and S1-S2 coupling interval), yielding a maximal slope of 1.6. On the other hand, APDR curve of P5-aligned substrates showed a slightly flattened curve with a maximum slope of 1.4. However, the difference was not statistically significant.

Figure 6:
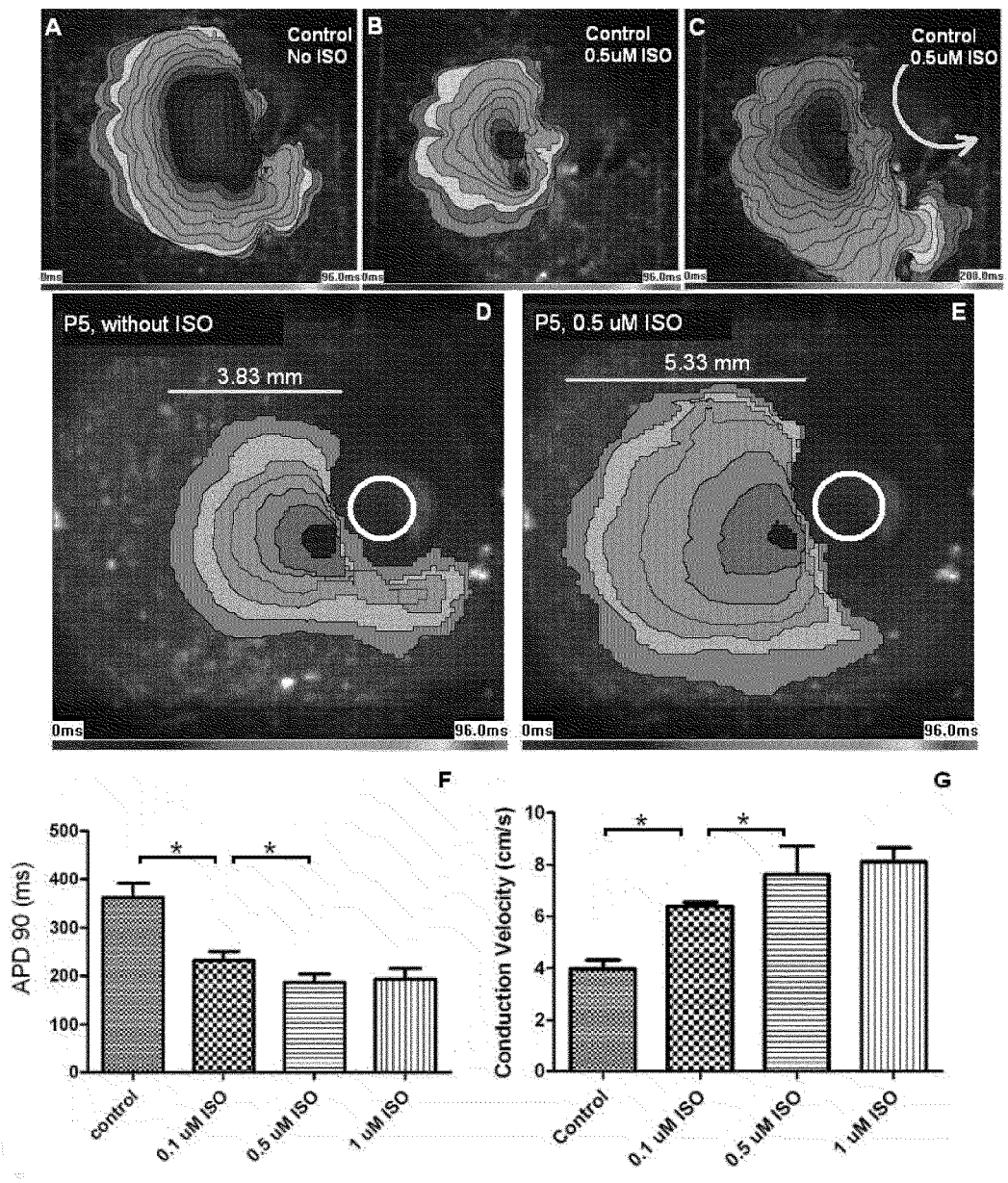
FIG. 6A-G show effects of isoproterenol on control (A-C) and P5-aligned (D, E) hESC-VCMs. Isoproterenol reduces AP duration (F), while increasing CV (G) and depolarization (upstroke) velocity, Spatiotemporal heterogeneity on control monolayer (A) is greatly augmented by 0.5 μM isoproterenol (B). Reentrant arrhythmia was induced on control substrates (C) by 0.5 μM isoproterenol. Despite of the increased conduction velocity as shown on isochrone maps (D-E), isoproterenol-induced augmentation of spatiotemporal heterogeneity is greatly reduced by aligned substrates. White circle indicates stimulation sites. Data are presented as mean±SD, with * denoting significant differences between the designated bars (p<0.01).

Alignment-Induced Anisotropy Reduces Spatial Dispersion and Pro-Arrhythmic Effect Promoted by Isoproterenol This example next studied the effect of the β-adrenergic agonist isoproterenol on control and aligned preparations. Monolayers that displayed neither spontaneous nor induced sustained reentrant arrhythmias were chosen for experiments. With steady-state pacing at 1 Hz, 0.1, 0.5 and 1.0 µM isoproterenol significantly increased the CV of control preparations to 6.3±1.4 cm/s, 7.6±1.1 cm is and 8.1±0.6 cm/s, respectively (n=3, $p<0.05$). Isochronal conduction maps revealed that isoproterenol augmented the spatial dispersion of CV as indicated by the irregularity and spread of isochrones compared to the typical circular pattern observed under isoproterenol-free baseline conditions (FIG. 6A-B). Consistent with a pro-arrhythmic effect, such dispersion increased the susceptibility to sustained functional reentrant arrhythmias by leading to spontaneous spiral waves in 2 of 3 (i.e., 66%) control preparations (FIG. 6C). In contrast, P5-induced alignment attenuated CV dispersion by 0.5 µM isoproterenol (FIG. 6D-E) despite the increase in T- and L-CVs from 2.89 cm/s and 4.98 cm/s to 4.91 cm/s and 7.76 cm/s, respectively; n=3). ARs before and after isoproterenol application were identical (1.83 and 1.76; n=2). At 0.5 µM, no sustained functional reentrant arrhythmias could be observed (n=2).

Cardiac tissue exhibits an orderly anisotropic organization that enables electrical and mechanical events to take place in a coordinated fashion for effective blood pumping. This example demonstrates that shrink-film microfabrication enables physical alignment of hESC-VCMs, thereby reproducing functional anisotropy; importantly, aligned anisotropic hESC-VCMs appear less susceptible to reentrant arrhythmias.

Structural and functional remodeling, including changes in anisotropy, occurs in pathological states (e.g., ischemia, infarction and heart failure) and contributes to arrhythmogenesis. In addition to cellular triggers, heterogeneity of cellular electrophysiology is a major contributing factor to sustained reentry and arrhythmias. Heterogeneity can be static or dynamic. For instance, the presence of mixed populations of cells with a range of functional properties could contribute to the spatial and temporal dispersion of refractoriness. in these experiments, a ventricular specification protocol that generates hESC-VCMs was employed to minimize phenotypic heterogeneity.

Also, internal comparison was made between control and aligned preparations of hESC-VCMs to confirm the functional consequences of physical alignment. As a means to introduce dynamic heterogeneity, this example performed programmed electrical stimulation to introduce a large premature stimulus for creating a wavebreak, which depends on the electrical restitution properties that are known to play a role in the transition to VF and its subsequent maintenance. Indeed, the steepness of APD restitution is a calcium-dependent parameter crucial for spiral wave stability.

As shown in these data, however, physical cellular alignment did not alter APD restitution. Taken together with the observation that cellular properties such as APD90 were not different between control and aligned preparations, the differences in AR and conduction properties as well as the reduced incidence of spontaneous and inducible arrhythmias could therefore be attributed to the physical alignment per se.

PSC-VCMs offer promising options for cell-based myocardial repairs to benefit patients with conditions such as heart failure (HF). The present results raise the intriguing possibility that the dynamic stability of PSC-derived grafts, which can be enhanced by cell alignment for a lower probability of reentrant arrhythmias, needs to be assessed before transplantation to patients with prominent pre-existing heterogeneity (e.g., HF) which likely further increases dispersion and therefore susceptibility to arrhythmias.

* * *

Thus, it should be understood that although the present disclosure has been specifically disclosed by preferred embodiments and optional features, modification, improvement and variation of the disclosure embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. An isolated population of cardiomyocytes prepared by a method comprising aligning stem cells on a three-dimensional concave, micro-textured surface and culturing the aligned stem cells under conditions suitable for the stem cells to differentiate into the isolated population of cardiomyocytes, wherein the three-dimensional concave, micro-textured surface 1) conforms to an interior surface of a balloon and 2) includes at least about 10% of a sphere, and wherein the population of cardiomyocytes produces functional anisotropy.

2. The isolated population of claim 1, wherein the population comprises ventricular cardiomyocytes.

3. The isolated population of claim 1, wherein the population comprises ventricular cardiomyocytes and fibroblasts.

4. The isolated population of claim 3, wherein the population comprises ventricular cardiomyocytes and fibroblasts at a ratio selected from the group consisting of 1:1; 2:1; and 1:2.

5. The isolated population of claim 1, wherein the surface is prepared by a method comprising soft-lithography of a plasma-treated micro-textured master with grooved surface features to impose contact guidance cues during chamber creation.

6. The isolated population of claim 5, wherein the stem cells are prepared by differentiating a composition comprising one or more of an embryonic stem cell, an induced pluripotent stem cell (iPSCs) and an adult stem cell.

7. The isolated population of claim 1, wherein the surface is prepared by a method comprising soft-lithography of a plasma-treated textured balloon with grooved surface features to impose contact guidance cues during chamber creation.

8. The isolated population of claim 7, wherein the stem cells are prepared by differentiating a composition comprising one or more of an embryonic stem cell, an induced pluripotent stem cell (iPSCs) and an adult stem cell.

9. The isolated population claim 1, wherein the stem cells are mammalian or human stem cells.

10. The isolated population of claim 9, wherein the stem cells are prepared by differentiating a composition comprising one or more of an embryonic stem cell, an induced pluripotent stem cell (iPSCs) and an adult stem cell.

11. The isolated population of claim 1, wherein the stem cells are prepared by differentiating a composition comprising one or more of an embryonic stem cell, an induced pluripotent stem cell (iPSCs) and an adult stem cell.

12. The isolated population of claim 1, wherein the stem cells are prepared by differentiating a composition comprising one or more of an embryonic stem cell, an induced pluripotent stem cell (iPSCs) and an adult stem cell.

13. A method of preparing an isolated population of cardiomyocytes, comprising aligning stem cells on a three-dimensional concave, micro-textured surface and culturing the aligned stem cells under conditions suitable for the stem cells to differentiate into the isolated population of cardiomyocytes, wherein the three-dimensional concave, micro-textured surface 1) conforms to an interior surface of a balloon and 2) includes at least about 10% of a sphere, and wherein the population of cardiomyocytes produces functional anisotropy.

14. The method of claim 13, further comprising, prior to culturing the stem cells on the textured surface, preparing the textured surface with a method comprising treating a thermoplastic material with plasma, shrinking the treated thermoplastic material to obtain a textured surface, replicating the textured surface using soft lithography to a scaffold to generate a textured surface on the scaffold, and subjecting the scaffold to a pressure to render the surface of the scaffold concave.

15. The method of claim 14, wherein the thermoplastic material is treated with the plasma for about 5 minutes.

16. The method of claim 14, wherein only one side of the thermoplastic material is treated with the plasma.

17. The method of claim 14, wherein the plasma is oxygen plasma.

18. The method of claim 14, wherein the aligned cardiomyocytes are ventricular myocytes.

19. The method of claim 18, wherein the aligned ventricular cardiomyocytes have at least one of a transverse conduction velocity of from about 2 to about 4 cm/s at 1 HZ or a longitudinal conduction velocity of from about 3 to 8 cm/s at 1 HZ.

20. The method of claim 18, wherein the aligned ventricular cardiomyocytes have an average anisotropy ratio (AR) of from about 0.5 to 1.5.

21. The method of claim 13, wherein the aligned cardiomyocytes are ventricular myocytes.

22. The method of claim 21, wherein the aligned ventricular cardiomyocytes have at least one of a transverse conduction velocity of from about 2 to about 4 cm/s at 1 HZ or a longitudinal conduction velocity of from about 3 to 8 cm/s at 1 HZ.

* * * * *